(12) United States Patent
Wang

(10) Patent No.: US 10,639,159 B2
(45) Date of Patent: May 5, 2020

(54) RETICULAR FIXATION SYSTEM FOR ARTICULAR CARTILAGE

(71) Applicant: Union Hospital, Tongji Medical College, Huazhong University of Science and Technology, Wuhan (CN)

(72) Inventor: Hong Wang, Wuhan (CN)

(73) Assignee: Union Hospital, Tongji Medical College, Huazhong University of Science and Technology, Wuhan (CN)

( * ) Notice: Subject to any disclaimer, the term of this patent is extended or adjusted under 35 U.S.C. 154(b) by 11 days.

(21) Appl. No.: 15/673,380

(22) Filed: Aug. 9, 2017

(65) Prior Publication Data

US 2019/0046320 A1 Feb. 14, 2019

(51) Int. Cl.
*A61F 2/30* (2006.01)
*A61F 2/46* (2006.01)
(Continued)

(52) U.S. Cl.
CPC ...... *A61F 2/30756* (2013.01); *A61B 17/0642* (2013.01); *A61B 17/88* (2013.01); *A61F 2/4618* (2013.01); *A61B 17/848* (2013.01); *A61B 2017/0641* (2013.01); *A61B 2017/90* (2013.01); *A61B 2017/922* (2013.01);
(Continued)

(58) Field of Classification Search
CPC ................ A61F 2/30756; A61F 2/4618; A61F 2002/30759; A61F 2002/30766; A61B 17/846; A61B 17/848
See application file for complete search history.

(56) References Cited

U.S. PATENT DOCUMENTS 5,067,964 A * 11/1991 Richmond .......... A61F 2/30756
 623/14.12
2007/0073394 A1 * 3/2007 Seedhom ............ A61F 2/30749
 623/14.12
(Continued)

FOREIGN PATENT DOCUMENTS

CN 202051804 U 11/2011
CN 203042422 U 7/2013
(Continued)

*Primary Examiner* — William H Matthews
(74) *Attorney, Agent, or Firm* — Wayne & Ken, LLC; Tony Hom

(57) ABSTRACT

The invention provides a reticular fixation system and method for an articular cartilage. The system comprises an articular cartilage repair surface locator, a temporary fixation kirschner wire, a depth-control guide wire, a percussion device and a cartilage fixing piece. The method comprises: repositing an injured articular cartilage; placing a locator on a surface of the injured articular cartilage; fixing the locator to the articular cartilage and the bone temporarily; punching the fixing piece wire tunnels on the articular cartilage and the bone in a fixing piece guide channel of the locator; placing the fixing piece into a fixing piece wire guide channel; percussing a fixing piece nail into the tunnels of the articular cartilage and the bone; removing the temporary fixation kirschner wire; implanting a second fixing piece nail, and completing the articular cartilage repair. The invention can improve convenience and reliability of fixation of the injured cartilage.

8 Claims, 11 Drawing Sheets

(51) Int. Cl.
  *A61B 17/88* (2006.01)
  *A61B 17/064* (2006.01)
  A61B 17/84 (2006.01)
  A61B 17/92 (2006.01)
  A61B 17/90 (2006.01)

(52) U.S. Cl.
  CPC .............. *A61F 2002/30062* (2013.01); *A61F 2002/30461* (2013.01); *A61F 2002/4677* (2013.01); *A61F 2002/4681* (2013.01); *A61F 2002/4687* (2013.01)

(56) References Cited

U.S. PATENT DOCUMENTS

2013/0085503 A1 4/2013 Smith et al.
2016/0250026 A1* 9/2016 Dee .................... A61F 2/30756
                                            623/20.16

FOREIGN PATENT DOCUMENTS

| CN | 104367356 A | 2/2015 |
| CN | 104434281 A | 3/2015 |
| CN | 205988322 U | 3/2017 |
| RU | 2269964 C2 | 2/2006 |

* cited by examiner

RETICULAR FIXATION SYSTEM FOR ARTICULAR CARTILAGE

TECHNICAL FIELD

The present invention relates to the technical field of medical apparatuses, and more specifically, to a reticular fixation system for an articular cartilage.

BACKGROUND OF THE INVENTION

Cartilage is an "apparatus" which acts as a cushion or a shock absorber in human joints, covering and protecting the joints. The cartilage plays a role of bearing load in the human body and can reduce bone friction between the joints. If protection of the cartilage is lost, direct friction and collision between bones may appear in the joints; as a result, joint pain, swelling and other symptoms may appear in the human body, followed by osteoarthritis.

During an orthopedic surgery, a situation of articular cartilage denudation is often found. In view of this situation, there is a lack of rapid and convenient treatment methods at present, and the denudated cartilage is removed in most cases. Because the cartilage is hard to regenerate, when a cartilage denudation area is large, if a cartilage block is removed, a patient easily suffers from degenerative arthritis after the surgery, which will seriously affect life of the patient.

SUMMARY OF THE INVENTION

The purpose of embodiments of the present invention is to provide a reticular fixation system and method for an articular cartilage, for effectively improving convenience and reliability of fixation of the articular cartilage.

In a first aspect, the reticular fixation system for the articular cartilage provided by embodiments of the present invention comprises an articular cartilage repair surface locator, a temporary fixation kirschner wire, a depth-control guide wire, a percussion device and a cartilage fixing piece. The articular cartilage repair surface locator comprises a top surface, a bottom surface and a side surface. The top surface and the bottom surface are arranged oppositely. The side surface is connected between the top surface and the bottom surface. A wire tip of the temporary fixation kirschner wire sequentially passes through the top surface and the bottom surface of the articular cartilage repair surface locator, is penetrated into the articular cartilage and a bone, and fixes the articular cartilage to an articular surface on which the articular cartilage is located. The depth-control guide wire is used to punch fixing piece wire tunnels on the articular cartilage and the bone. The cartilage fixing piece is used to fix the articular cartilage to the articular surface on which the articular cartilage is located. The percussion device is used to nail the cartilage fixing piece into the articular surface.

A guide channel penetrating through the articular cartilage repair surface locator is arranged along a length direction of the articular cartilage repair surface locator. The shape and size of the guide channel matches with the cartilage fixing piece. The depth-control guide wire can be moved along the length direction of the articular cartilage repair surface locator in the guide channel. The cartilage fixing piece can be moved along the length direction of the articular cartilage repair surface locator in the guide channel. The length of the percussion device is greater than or equal to that of the articular cartilage repair surface locator.

Preferably, a handle is arranged at a position on the side surface of the articular cartilage repair surface locator close to the top surface. The handle and the articular cartilage repair surface locator are integrally formed.

Preferably, a portion between a nail head and a nail cap of the cartilage fixing piece is a smooth structure, a frosted structure or a barbed structure.

Preferably, the depth-control guide wire is made of a metallic material and comprises an upper section and a lower section. A depth-control apparatus is arranged between the upper section and the lower section. The upper section, the lower section and the depth-control apparatus are integrally formed. A main body of the depth-control guide wire is columnar, and a lower end is pointed. The depth-control apparatus comprises a columnar surface perpendicular to the main body of the depth-control guide wire, a disk-like surface perpendicular to the main body of the depth-control guide wire and the like.

Preferably, the cartilage fixing piece is made of an absorbable organic material, and can also be made of a PK material and a metallic material. The absorbable material comprises polyglycolide, polylactide and polyamide.

Preferably, the cartilage fixing piece comprises a plurality of fixing nails and a connecting piece for connecting the plurality of fixing nails to each other. The connecting piece is made of an absorbable material. The absorbable material comprises a catgut, a macromolecular chemical synthesis line, a pure natural collagen suture, polyglycolide, polylactide and polyamide.

Preferably, the plurality of fixing nails are connected to each other by the connecting piece to form a mesh. The mesh comprises triangles, straight sections, crosses and polygons.

Preferably, the articular cartilage repair surface locator and the percussion device are made of plastic or metallic materials.

Preferably, an arc structure consistent with the articular surface is arranged between the bottom surface and the side surface of the articular cartilage repair surface locator.

Preferably, the articular cartilage repair surface locator is provided with a graduated scale. Scale lines of the graduated scale are arranged along the length direction of the articular cartilage repair surface locator.

In a second aspect, a method for fixing an articular cartilage provided by embodiments of the present invention is applied to the reticular fixation system for the articular cartilage. The system comprises an articular cartilage repair surface locator, a temporary fixation kirschner wire, a percussion device and a cartilage fixing piece. The articular cartilage repair surface locator comprises a top surface, a bottom surface and a side surface. The top surface and the bottom surface are arranged oppositely. The side surface is connected between the top surface and the bottom surface. A wire tip of the temporary fixation kirschner wire sequentially passes through the top surface and the bottom surface of the articular cartilage repair surface locator, is penetrated into the articular cartilage and a bone, and fixes the articular cartilage to an articular surface on which the articular cartilage is located. A depth-control guide wire is used to punch fixing piece wire tunnels on the articular cartilage and the bone. The cartilage fixing piece is used to fix the articular cartilage to the articular surface on which the articular cartilage is located. The percussion device is used to nail the cartilage fixing piece into the articular surface, wherein a guide channel penetrating through the articular cartilage repair surface locator is arranged along a length direction of the articular cartilage repair surface locator. The guide channel is matched with the cartilage fixing piece in shape and size. The cartilage fixing piece can be moved along the length direction of the articular cartilage repair surface locator in the guide channel. The length of the percussion device is greater than or equal to that of the articular cartilage repair surface locator.

The method comprises the following steps: repositing an injured articular cartilage firstly; placing a locator on a surface of the injured articular cartilage; fixing the locator to the articular cartilage and the bone temporarily by the temporary fixation kirschner wire in a fixing hole; punching the fixing piece wire tunnels on the articular cartilage and the bone in a fixing piece guide channel of the locator by the depth-control guide wire; placing the fixing piece into a fixing piece wire guide channel; percussing a fixing piece nail into the tunnels of the articular cartilage and the bone by the percussion device; removing the temporary fixation kirschner wire; and implanting a second fixing piece nail in the same method, and completing the articular cartilage repair.

According to the reticular fixation system and method for the articular cartilage provided by embodiments of the present invention, the wire tip of the temporary fixation kirschner wire sequentially passes through the top surface and the bottom surface of the articular cartilage repair surface locator, is penetrated into the articular cartilage and the bone, and fixes the articular cartilage to the articular surface on which the articular cartilage is located; the depth-control guide wire is used to punch the fixing piece wire tunnels on the articular cartilage and the bone; the articular cartilage is fixed to the articular surface on which the articular cartilage is located by the cartilage fixing piece; and the percussion device is used to nail the cartilage fixing piece into the articular surface, so as to fix the articular cartilage reliably and implement the fixation more conveniently.

BRIEF DESCRIPTION OF DRAWINGS

In view of this, designers of the present invention design a reticular fixation system and method for an articular cartilage through long-term exploration and attempt, many experiments and efforts and continuous reform and innovation, so that the articular cartilage can be fixed conveniently and reliably.

In order to illustrate technical solutions of embodiments of the present invention more clearly, drawings to be used in embodiments are briefly described below. It should be understood that the following drawings only show some embodiments of the present invention, and should not be construed as a limitation to the scope. Those ordinary skilled in the art can also acquire other relevant drawings according to these drawings without contributing creative work.

Figure 1:
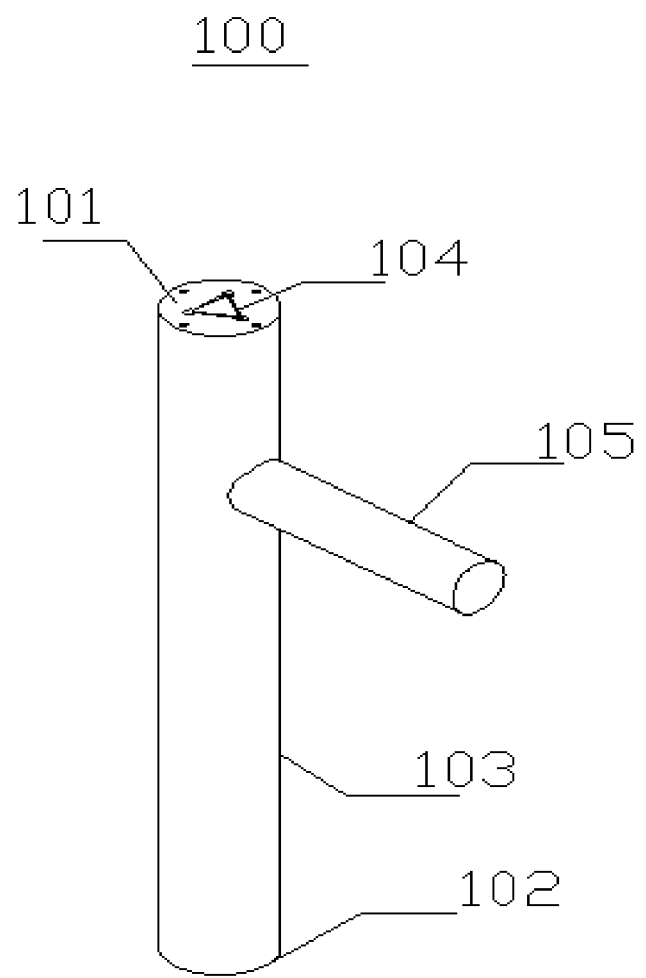
FIG. 1 is a structural schematic diagram of an articular cartilage repair surface locator in a reticular fixation system for an articular cartilage provided by embodiments of the present invention.

Reference numerals in the drawings are:

articular cartilage repair surface locator 100; temporary fixation kirschner wire 200; percussion device 300; cartilage fixing piece 400; articular surface 500; articular cartilage 600 and depth-control guide wire 700;

top surface 101; bottom surface 102; side surface 103; guide channel 104 and handle 105.

DETAILED DESCRIPTION OF THE INVENTION

In order to make purposes, technical solutions and advantages of embodiments of the present invention clearer, the technical solutions in embodiments of the present invention are clearly and completely described below with reference to drawings in embodiments of the present invention. Apparently, the described embodiments are part of embodiments of the present invention, and not all embodiments. All other embodiments acquired by those ordinary skilled in the art without contributing creative work based on embodiments in the present invention belong to a protection scope of the present invention. Thus, the following detailed description of embodiments of the present invention provided in the drawings is not intended to limit the protection scope of the present invention, but merely represents the selected embodiments of the present invention.

It should be understood in the description of the present invention that terms such as "center", "longitudinal", "transverse", "length", "width", "thickness", "upper", "lower", "front", "rear", "left", "right", "vertical", "horizontal", "top", "bottom", "inner", "outer", "clockwise", "counterclockwise" and the like indicate direction or position relationships shown based on the drawings, and are only intended to facilitate the description of the present application and simplify the description rather than to indicate or imply that the indicated device or element must have a specific direction or be constructed and operated in a specific direction, and therefore, shall not be understood as a limitation to the present application.

In addition, the terms such as "first" and "second" are only used for the purpose of description, rather than being understood to indicate or imply relative importance or hint the number of indicated technical features. Thus, the features limited by "first" and "second" can explicitly or implicitly comprise one or more features. In the description of the present application, the meaning of "a plurality of" is two or more unless otherwise specified.

It should be noted that similar reference numerals and letters denote similar items in the following drawings, and therefore, once an item is defined in a drawing, it is unnecessary to further define and explain it in the subsequent drawings.

Figure 2:
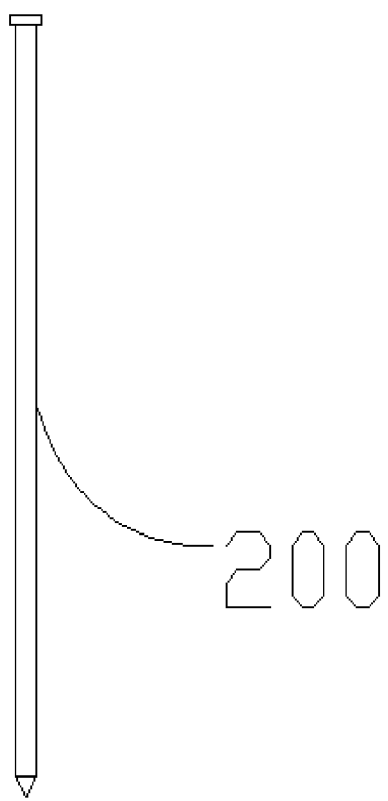
FIG. 2 is a structural schematic diagram of a temporary fixation kirschner wire in a reticular fixation system for an articular cartilage provided by embodiments of the present invention.
Figure 3:
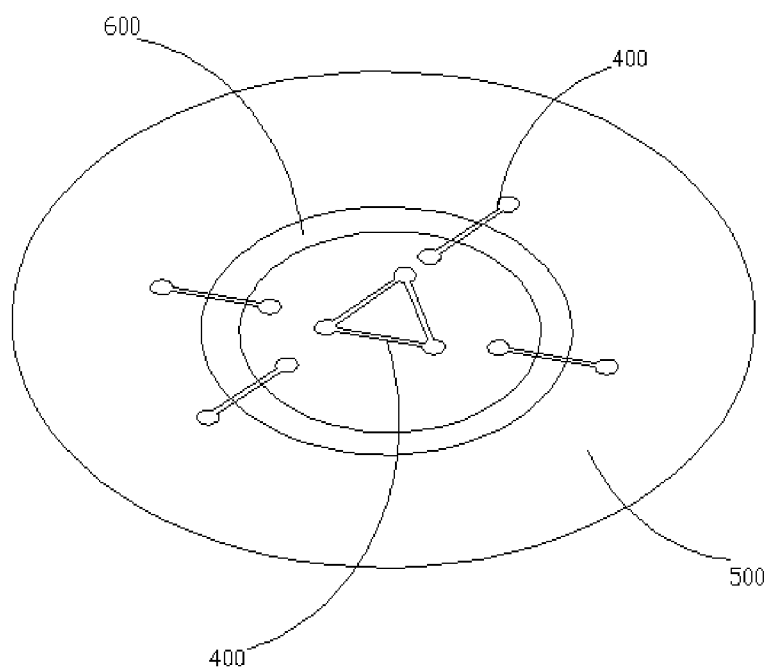
FIG. 3 is a schematic diagram of installation when a reticular fixation system for an articular cartilage provided by embodiments of the present invention is implemented.
Figure 4:
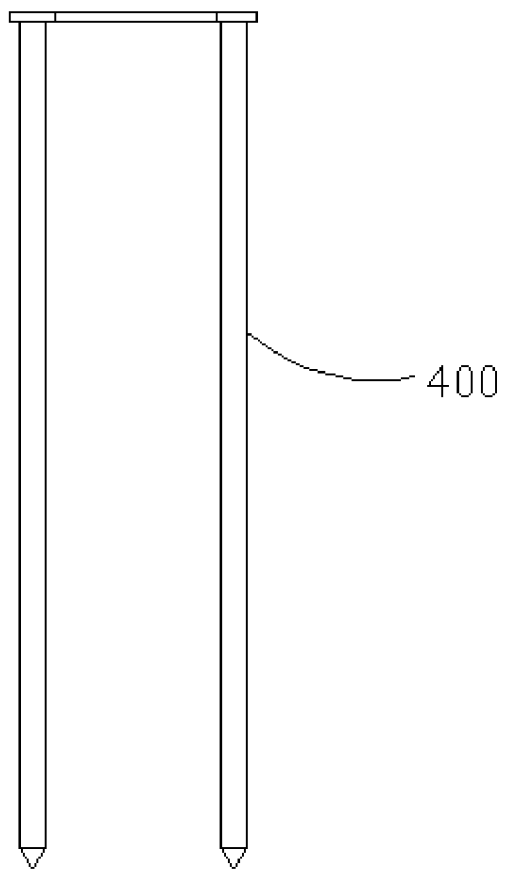
FIG. 4 is a structural schematic diagram of a cartilage fixing piece in a reticular fixation system for an articular cartilage provided by embodiments of the present invention.
Figure 5:
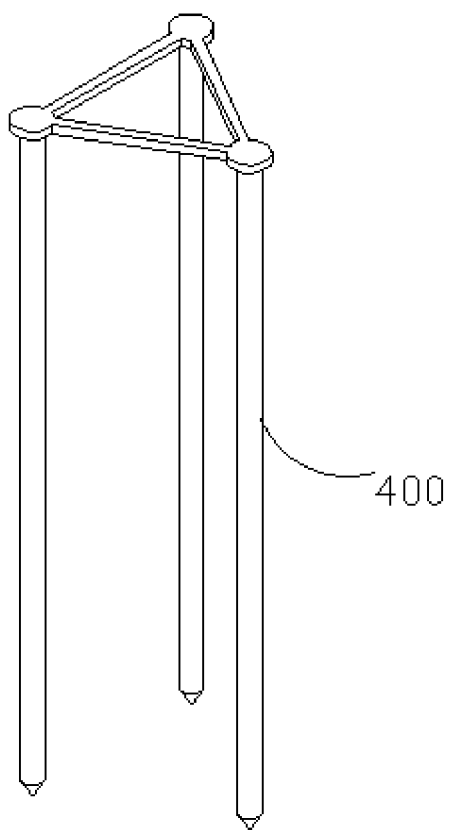
FIG. 5 is another structural schematic diagram of a cartilage fixing piece in a reticular fixation system for an articular cartilage provided by embodiments of the present invention.
Figure 6:
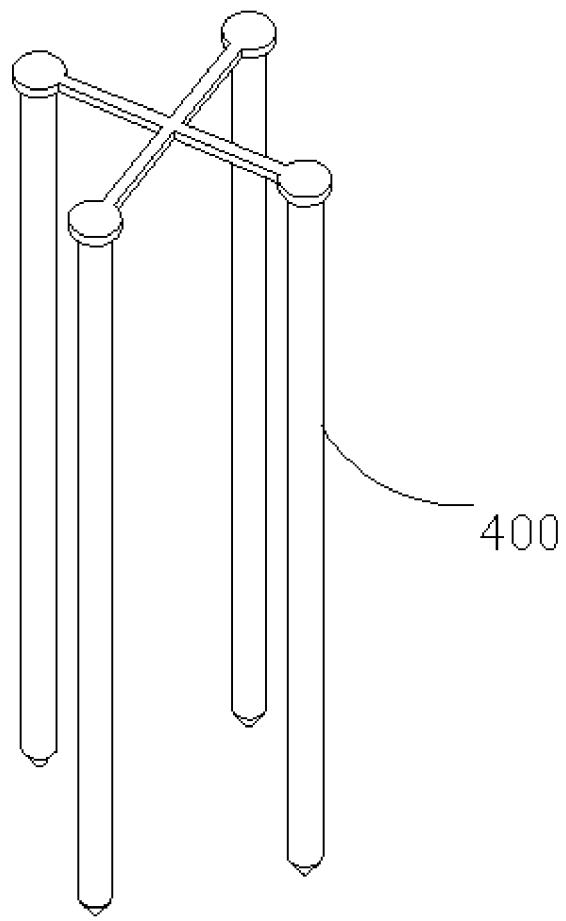
FIG. 6 is another structural schematic diagram of a cartilage fixing piece in a reticular fixation system for an articular cartilage provided by embodiments of the present invention.
Figure 8:
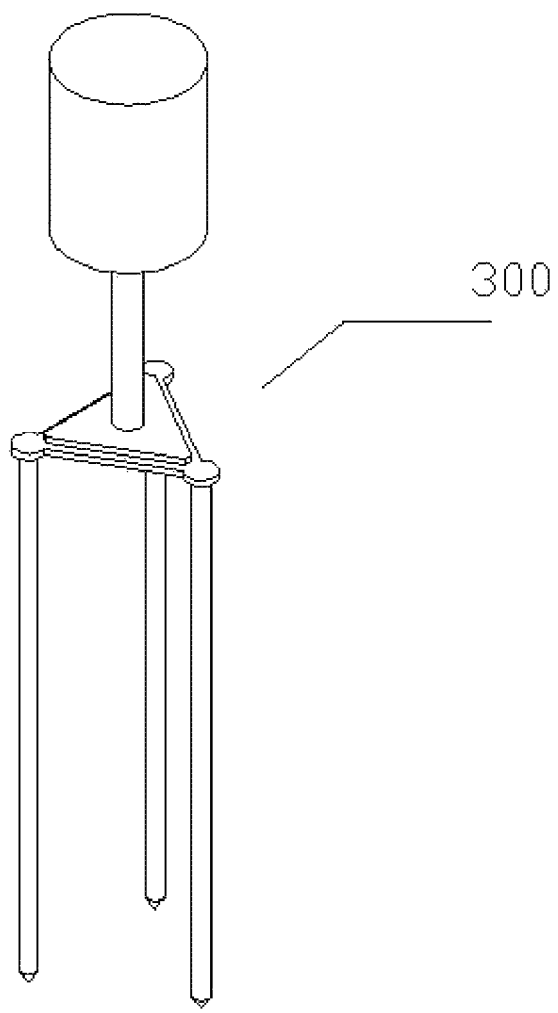
FIG. 8 is a schematic diagram of a percussion device in a reticular fixation system for an articular cartilage provided by embodiments of the present invention.

Embodiments of the present invention provide a reticular fixation system for an articular cartilage. The system mainly comprises an articular cartilage repair surface locator 100, a temporary fixation kirschner wire 200, a percussion device 300, a cartilage fixing piece 400 and a depth-control guide wire 700. The system can be used not only for cartilage repair, but also for rotator cuff injury repair, tendon end fixation, fracture fixation and the like. As shown in FIG. 1, the articular cartilage repair surface locator 100 comprises a top surface 101, a bottom surface 102 and a side surface 103. Optionally, the articular cartilage repair surface locator 100 is a cylinder. The top surface 101 and the bottom surface 102 of the articular cartilage repair surface locator 100 are arranged oppositely and parallel to each other. The top surface 101 and the bottom surface 102 are circular. The side surface 103 is connected between the top surface 101 and the bottom surface 102. A cross section of the side surface 103 is rectangular, and the width of the rectangle is equal to perimeters of the top surface 101 and the bottom surface 102. FIG. 2 is a structural schematic diagram of the temporary fixation kirschner wire 200. A wire tip of the temporary fixation kirschner wire 200 sequentially passes through the top surface 101, the side surface 103 and the bottom surface 102 of the articular cartilage repair surface locator 100, and is penetrated into an articular cartilage 600 and a bone in contact with the bottom surface 102, so as to fix the articular cartilage 600 to an articular surface 500 on which the articular cartilage 600 is located, with reference to FIG. 3. In this manner, the initial fixation of the articular cartilage 600 and the articular surface 500 on which the articular cartilage 600 is located is achieved. The depth-control guide wire 700 sequentially passes through the top surface 101, the side surface 103 and the bottom surface 102 of the articular cartilage repair surface locator 100, and is penetrated into the articular cartilage 600 and the bone in contact with the bottom surface 102, so as to punch fixing piece wire tunnels on the articular cartilage 600 and the bone. Similarly, the cartilage fixing piece 400 sequentially passes through the top surface 101, a cylinder body and the bottom surface 102 of the articular cartilage repair surface locator 100, and is penetrated into the articular cartilage 600 in contact with the bottom surface 102, so as to fix the articular cartilage 600 to the articular surface 500 on which the articular cartilage 600 is located. Optionally, as shown in FIG. 4 to FIG. 6, the shape of the cartilage fixing piece 400 may comprise a triangle, a door shape, a cross, a polygon and the like. A lower end of the cartilage fixing piece 400 is pointed. In this manner, the final fixation of the articular cartilage 600 and the articular surface 500 on which the articular cartilage 600 is located is achieved. FIG. 8 is a schematic diagram of the percussion device 300. The percussion device 300 is used to nail the cartilage fixing piece 400 into the articular surface 500.

During implementation, in order to facilitate the percussion device 300 to nail the cartilage fixing piece 400 into the articular surface 500, a guide channel 104 is arranged in the articular cartilage repair surface locator 100. The guide channel 104 is arranged to be hollowed, and the guide channel 104 is matched with the cartilage fixing piece 400 in shape and size, so that the cartilage fastener 400 can be placed into the guide channel 104 exactly. It should be understood that the guide channel 104 is arranged along a length direction of the articular cartilage repair surface locator 100, and the guide channel 104 penetrates through the top surface 101 and the bottom surface 102 of the articular cartilage repair surface locator 100. In this manner, the cartilage fixing piece 400 can be moved along the length direction of the articular cartilage repair surface locator 100 in the guide channel 104. In order to make the percussion device 300 nail the cartilage fixing piece 400 into the articular surface 500 successfully, the length of the percussion device 300 is configured to be greater than or equal to that of the articular cartilage repair surface locator 100.

Further, a handle 105 is arranged on the side surface 103 of the articular cartilage repair surface locator 100. The handle 105 is located at a position close to the top surface 101. The handle 105 and the articular cartilage repair surface locator 100 are integrally formed, wherein the articular cartilage repair surface locator 100 and the handle 105 are made of plastic or metallic materials. When the articular cartilage repair surface locator 100 and the handle 105 are made of the plastic materials, the handle 105 is connected to the articular cartilage repair surface locator 100 in a hot-melting manner. When the articular cartilage repair surface locator 100 and the handle 105 are made of the metallic materials, the handle 105 is connected to the articular cartilage repair surface locator 100 in a welding manner. When the percussion device 300 is used to fix the articular cartilage 600 to the articular surface 500 on which the articular cartilage 600 is located, the convenience for using the percussion device 300 can be improved by gripping the handle 105 arranged on the side surface 103 of the articular cartilage repair surface locator 100. The percussion device 300 is made of a plastic or metallic material.

Figure 7:
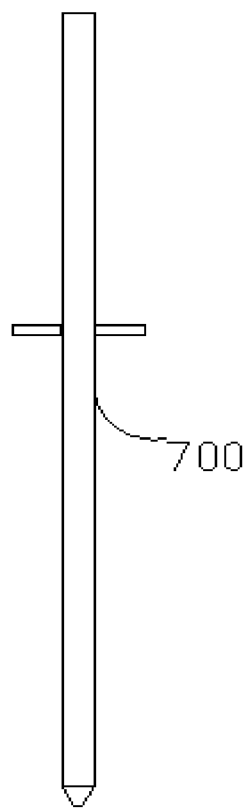
FIG. 7 is a structural schematic diagram of a depth-control guide wire in a reticular fixation system for an articular cartilage provided by embodiments of the present invention.

Further, as shown in FIG. 7, the depth-control guide wire 700 comprises an upper section and a lower section. A depth-control apparatus is arranged between the upper section and the lower section. The upper section, the lower section and the depth-control apparatus are integrally formed. A main body of the depth-control guide wire 700 is columnar, and a lower end is pointed. The depth-control apparatus comprises a columnar surface perpendicular to the main body of the depth-control guide wire 700, a disk-like surface perpendicular to the main body of the depth-control guide wire 700 and the like. The length of the lower portion of the depth-control guide wire 700 is equal to the sum of the length of the articular cartilage repair surface locator 100 and the length of the cartilage fixing piece 400. The length of the upper section is not limited. A diameter of the depth-control guide wire 700 is consistent with that of the cartilage fixing piece 400. During implementation, the depth-control guide wire 700 sequentially passes through the top surface 101, the side surface 103 and the bottom surface 102 of the articular cartilage repair surface locator 100, and is penetrated into the articular cartilage 600 and the bone in contact with the bottom surface 102, so as to punch the fixing piece wire tunnels on the articular cartilage 600 and the bone. The depth-control guide wire 700 is clamped on an upper end surface of the articular cartilage repair surface locator 100 to play a role of controlling the depth, thereby facilitating the further fixation of the cartilage fixing piece 400.

Further, the cartilage fixing piece 400 may comprise a nail head and a nail cap. Depending on different needs in actual use, different structures are arranged between the nail head and the nail cap. For example, the structures may comprise a smooth structure, a frosted structure or a barbed structure. The smooth structure allows the cartilage fixing piece 400 to successfully pass through the top surface 101 and the bottom surface 102 of the articular cartilage repair surface locator 100. The frosted structure and the barbed structure allow the cartilage fixing piece 400 to fix the articular cartilage repair surface locator 100 and the articular cartilage 600, thereby fixing the articular cartilage 600 and the articular surface 500 on which the articular cartilage 600 is located.

In order to avoid removing the cartilage fixing piece 400 from the articular surface 500 on which the articular cartilage 600 is located after fixing the articular cartilage 600 to the articular surface 500 on which the articular cartilage 600 is located on the cartilage fixing piece 400, the cartilage fixing piece 400 is made of an absorbable organic material, and can also be made of a PK material and a metallic material. The absorbable material comprises polyglycolide, polylactide and polyamide, and therefore, the cartilage fixing piece 400 can be absorbed by the human body.

Figure 9:
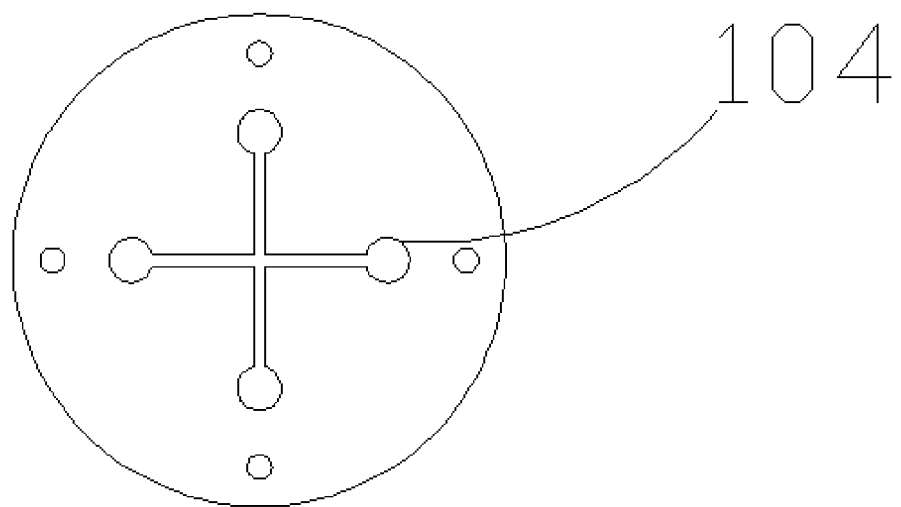
FIG. 9 is a structural schematic diagram of a guide channel in a reticular fixation system for an articular cartilage provided by embodiments of the present invention.
Figure 10:
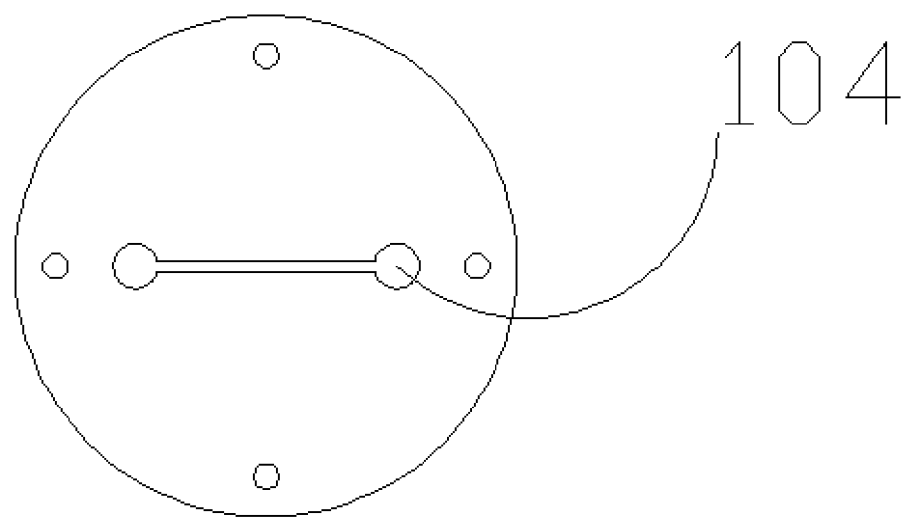
FIG. 10 is another structural schematic diagram of a guide channel in a reticular fixation system for an articular cartilage provided by embodiments of the present invention.
Figure 11:
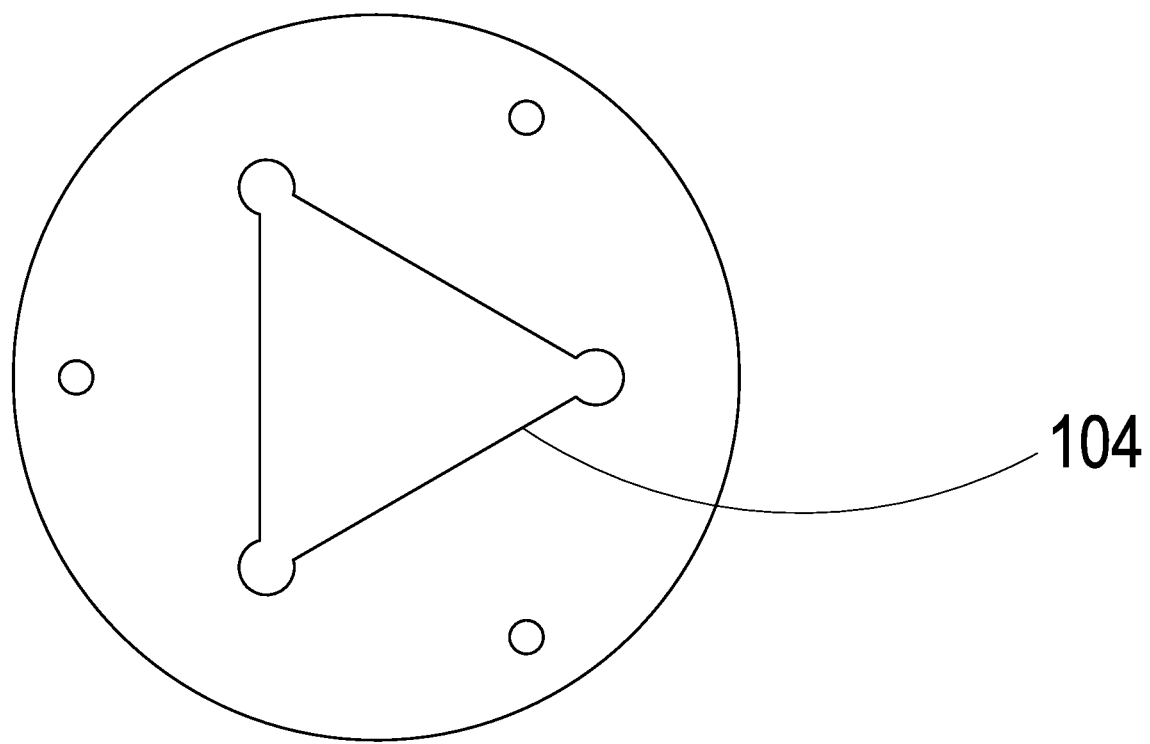
FIG. 11 is another structural schematic diagram of a guide channel in a reticular fixation system for an articular cartilage provided by embodiments of the present invention.

Further, the cartilage fixing piece 400 mainly comprises a plurality of fixing nails and a connecting piece. The connecting piece is used for connecting the plurality of fixing nails. The plurality of fixing nails form a mesh under action of the connecting piece. The mesh may comprise crosses, door shapes, triangles or other polygons, with reference to FIG. 9 to FIG. 11. A mesh-shaped structure allows the cartilage fixing piece 400 to better fix the articular cartilage 600 and the articular surface 500 on which the articular cartilage 600 is located. Similarly, in order to avoid removing the connecting piece from the articular surface 500 on which the articular cartilage 600 is located, the connecting piece is made of an absorbable material. Optionally, the absorbable material comprises a catgut, a macromolecular chemical synthesis line, a pure natural collagen suture, polyglycolide, polylactide, polyamide and the like, and therefore, the connecting piece can be absorbed by the human body.

During implementation, an arc structure is arranged at a transition position between the bottom surface 102 and the side surface 103 of the articular cartilage repair surface locator 100. The shape of the arc structure is consistent with that of the articular surface 500. In this manner, the articular cartilage 600 can be better contacted with the articular surface 500 on which the articular cartilage 600 is located, and the articular cartilage 600 can be conveniently fixed to the articular surface 500 on which the articular cartilage 600 is located by using the temporary fixation kirschner wire 200 and the cartilage fixing piece 400.

Further, in order to facilitate observation of the length of the articular cartilage repair surface locator 100 extending into the articular cartilage 600, a graduated scale is arranged on the articular cartilage repair surface locator 100. Scale lines of the graduated scale are arranged along the length direction of the articular cartilage repair surface locator 100. Optionally, the scale lines comprise a plurality of long lines and short lines alternately arranged along the length direction of the articular cartilage repair surface locator 100, for facilitating observation and reading by a user. A distance between the adjacent long line and short line may be 1 mm.

Embodiments of the present invention provide a method for fixing the articular cartilage 600, which is applied to the reticular fixation system for the articular cartilage.

Specifically, the method for fixing the articular cartilage comprises the following steps:

Step 1: abutting the bottom surface 102 of the articular cartilage repair surface locator 100 against the articular cartilage 600 so that the bottom surface 102 of the articular cartilage repair surface locator 100 is attached to the articular cartilage 600; adjusting the position of the articular cartilage repair surface locator 100, and abutting the articular cartilage 600 against the articular surface 500 on which the articular cartilage 600 is located.

Step 2: passing the wire tip of the temporary fixation kirschner wire 200 sequentially through the top surface 101 and the bottom surface 102 of the articular cartilage repair surface locator 100 along the length direction of the articular cartilage repair surface locator 100, and penetrating into the articular cartilage 600 and the bone; and fixing the articular cartilage 600 to the articular surface 500 on which the articular cartilage 600 is located, thereby realizing the initial fixation of the articular cartilage 600 and the articular surface 500 on which the articular cartilage 600 is located.

Step 3: passing the depth-control guide wire 700 sequentially through the top surface 101, the side surface 103 and the bottom surface 102 of the articular cartilage repair surface locator 100 and penetrating into the articular cartilage 600 and the bone in contact with the bottom surface 102, so as to punch fixing piece wire tunnels on the articular cartilage 600 and the bone.

Step 4: placing the cartilage fixing piece 400 into the guide channel 104 of the articular cartilage repair surface locator 100; using the percussion device 300 to make the cartilage fixing piece 400 sequentially pass through the top surface 101 and the bottom surface 102 of the articular cartilage repair surface locator 100 and nail the cartilage fixing piece 400 into the tunnels of the cartilage and the bone manufactured by the depth-control guide wire 700; and fixing the articular cartilage 600 to the articular surface 500 on which the articular cartilage 600 is located, thereby realizing the final fixation of the articular cartilage 600 and the articular surface 500 on which the articular cartilage 600 is located.

Step 5: withdrawing the temporary fixation kirschner wire 200 from the articular surface 500 and the articular cartilage 600; and then removing the articular cartilage repair surface locator 100 from the articular cartilage 600.

According to the reticular fixation system and method for the articular cartilage provided by embodiments of the present invention, the wire tip of the temporary fixation kirschner wire 200 sequentially passes through the top surface 101 and the bottom surface 102 of the articular cartilage repair surface locator 100 and then is penetrated into the articular cartilage 600 and the bone, and then the articular cartilage 600 is fixed to the articular surface 500 on which the articular cartilage 600 is located; the tunnels of the cartilage and the bone are manufactured by the depth-control guide wire 700; the articular cartilage 600 is fixed to the articular surface 500 on which the articular cartilage 600 is located by the cartilage fixing piece 400; and the percussion device 300 is used to nail the cartilage fixing piece 400 into the articular surface 500 so as to fix the articular cartilage 600 reliably and implement the fixation more conveniently, which can effectively reduce possibility of degenerative arthritis in the postoperative patients.

In the present invention, unless otherwise specifically regulated and defined, the terms such as "installation", "connected", "connection", "fixation" and the like should be understood in broad sense, and for example, may refer to fixed connection or detachable connection or integral connection, may refer to mechanical connection or electrical connection, may refer to direct connection or indirect connection through an intermediate medium, and may refer to inner communication of two elements or interaction of the two elements. For those ordinary skilled in the art, the specific meanings of the above terms in the present invention may be understood according to specific conditions.

In the present invention, unless otherwise specifically regulated and defined, a first feature is "above" or "below" a second feature may denote that the first feature is in direct contact with the second feature, and may also denote that the first feature is not in direct contact with the second feature but is in contact with the second feature through another feature between them. Moreover, the first feature is "above", "over" and "on" the second feature denotes that the first feature is right above or obliquely above the second feature, or only denotes that a horizontal height of the first feature is greater than that of the second feature. The first feature is "below", "under" and "beneath" the second feature denotes that the first feature is right below and obliquely below the second feature, or only denotes that the horizontal height of the first feature is smaller than that of the second feature.

The above contents are only preferred embodiments of the present invention and are not intended to limit the present invention. Various modifications and changes may be made to the present invention for those skilled in the art. Any modification, equivalent substitution, improvement and the like made within spirits and principles of the present invention should be included in the protection scope of the present invention.

What is claimed is:

1. A reticular fixation system for an articular cartilage, comprising:
    an articular cartilage repair surface locator;
    a temporary fixation kirschner wire;
    a depth-control guide wire;
    a percussion device; and
    a cartilage fixing piece;
    wherein the articular cartilage repair surface locator comprises a top surface, a bottom surface and a side surface; the top surface and the bottom surface are arranged oppositely; the side surface is connected between the top surface and the bottom surface; a wire tip of the temporary fixation kirschner wire sequentially passes through the top surface and the bottom surface of the articular cartilage repair surface locator; the depth-control guide wire is used to punch fixing piece wire tunnels; and the percussion device is used to nail the cartilage fixing piece;
    wherein a guide channel penetrating through the articular cartilage repair surface locator is arranged along a length direction of the articular cartilage repair surface locator; the guide channel fits the cartilage fixing piece; the cartilage fixing piece moves along the length direction of the articular cartilage repair surface locator in the guide channel;
    and the length of the percussion device is greater than or equal to that of the articular cartilage repair surface locator.

2. The reticular fixation system for the articular cartilage according to claim 1, wherein a handle is arranged at a position on the side surface and between the top surface and a middlepoint of the articular cartilage repair surface locator, and the handle and the articular cartilage repair surface locator are integrally formed.

3. The reticular fixation system for the articular cartilage according to claim 1, wherein a portion between a nail head and a nail cap of the cartilage fixing piece is a smooth structure, a frosted structure or a barbed structure.

4. The reticular fixation system for the articular cartilage according to claim 1, wherein the cartilage fixing piece is made of an absorbable organic material.

5. The reticular fixation system for the articular cartilage according to claim 4, wherein the cartilage fixing piece comprises a plurality of fixing nails and a connecting piece for connecting the plurality of fixing nails to each other; the connecting piece is made of an absorbable material; and the absorbable material is selected from the group consisting of a catgut, a macromolecular chemical synthesis line, a pure natural collagen suture, polyglycolide, polylactide and polyamide.

6. The reticular fixation system for the articular cartilage according to claim 5, wherein the plurality of fixing nails are connected to each other by the connecting piece to form a mesh, and a shape of the mesh is selected from the group consisting of triangle, straight section or polygon.

7. The reticular fixation system for the articular cartilage according to claim 1, wherein the articular cartilage repair surface locator and the percussion device are made of plastic or metallic materials.

8. A reticular fixation method for fixing an articular cartilage applied to a reticular fixation system for the articular cartilage, wherein the system comprises an articular cartilage repair surface locator, a temporary fixation kirschner wire, a depth-control guide wire, a percussion device and a cartilage fixing piece; the articular cartilage repair surface locator comprises a top surface, a bottom surface and a side surface; the top surface and the bottom surface are arranged oppositely; the side surface is connected between the top surface and the bottom surface; a wire tip of the temporary fixation kirschner wire sequentially passes through the top surface and the bottom surface of the articular cartilage repair surface locator; the depth-control guide wire is used to punch fixing piece wire tunnels; the percussion device is used to nail the cartilage fixing piece, wherein a guide channel penetrating through the articular cartilage repair surface locator is arranged along a length direction of the articular cartilage repair surface locator; the guide channel fits the cartilage fixing piece; the cartilage fixing piece can be moved along the length direction of the articular cartilage repair surface locator in the guide channel; and the length of the percussion device is greater than or equal to the length of the articular cartilage repair surface locator;
    the method comprises the following steps:
    repositing an injured articular cartilage firstly;
    placing the articular cartilage repair surface locator on a surface of the injured articular cartilage;
    fixing the articular cartilage repair surface locator to the articular cartilage and a bone temporarily by the temporary fixation kirschner wire in a fixing hole;
    punching the fixing piece wire tunnels into the articular cartilage and the bone in the guide channel by the depth-control guide wire;
    placing the cartilage fixing piece into the guide channel;
    percussing the cartilage fixing piece into the fixing piece wire tunnels by the percussion device; removing the temporary fixation kirschner wire; and
    placing another cartilage fixing piece into the guide channel;
    percussing the another cartilage fixing piece into the fixing piece wire tunnels by the percussion device;
    and completing the articular cartilage repair.

* * * * *